United States Patent
Gordon, III et al.

(10) Patent No.: US 7,773,725 B2
(45) Date of Patent: Aug. 10, 2010

(54) MULTI-ENERGY RADIOGRAPHY USING MONOENERGETIC PULSED SOURCE

(75) Inventors: Clarence L. Gordon, III, Renton, WA (US); Richard H. Bossi, Renton, WA (US); John L. Adamski, Kenmore, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 12/259,753

(22) Filed: Oct. 28, 2008

(65) Prior Publication Data

US 2010/0104072 A1 Apr. 29, 2010

(51) Int. Cl.
H05G 1/64 (2006.01)

(52) U.S. Cl. .................. 378/98.12; 378/98.9; 378/57; 378/53

(58) Field of Classification Search ............... 378/98.9, 378/98.11, 98.12, 53, 57, 62, 98.8
See application file for complete search history.

(56) References Cited

U.S. PATENT DOCUMENTS

| | | | |
|---|---|---|---|
| 5,042,055 | A | 8/1991 | Wirt et al. |
| 5,870,450 | A | 2/1999 | Khutoryansky et al. ..... 378/119 |
| 6,229,872 | B1 | 5/2001 | Amos |
| 6,256,372 | B1 | 7/2001 | Aufrichtig et al. ............ 378/41 |
| 6,333,966 | B1 | 12/2001 | Schoen |
| 6,873,677 | B2 | 3/2005 | Kaufman |
| 7,031,429 | B2 | 4/2006 | Akagi |
| 7,127,090 | B2 | 10/2006 | Kreang-Arekul et al. |
| 7,187,753 | B2 | 3/2007 | Freudenberger et al. |
| 7,236,564 | B2 | 6/2007 | Hopkins et al. |
| 7,280,636 | B2 | 10/2007 | Morrison et al. |
| 7,310,408 | B2 | 12/2007 | Filkins et al. ............... 378/197 |
| 7,321,604 | B2 | 1/2008 | Umstadter et al. |
| 7,356,115 | B2 | 4/2008 | Ford et al. |
| 7,412,025 | B1 | 8/2008 | Bossi et al. |
| 7,522,755 | B2 | 4/2009 | Li et al. |
| 2002/0057760 | A1 | 5/2002 | Carroll et al. |
| 2002/0094062 | A1* | 7/2002 | Dolazza et al. ............ 378/98.9 |
| 2003/0026469 | A1 | 2/2003 | Kreang-Arekul et al. |

(Continued)

OTHER PUBLICATIONS

Coumans, "Duel-energy X-ray Diagnostics," Philips Tech. Rev. 42, No. 8/9 pp. 274-285, Jun. 24, 1986.

(Continued)

*Primary Examiner*—Courtney Thomas
(74) *Attorney, Agent, or Firm*—Yee & Associates, P.C.; Dennis R. Plank

(57) ABSTRACT

A method and apparatus for multi-energy object inspection using a brilliant x-ray source. A first mono-energetic x-ray image of an object at a first selected energy is generated. A second mono-energetic x-ray image of the object at a second selected energy is generated. The first selected energy is different than the second selected energy. Additional mono-energetic x-ray images may be generated at energies different than previous energies up to n selected energies. The mono-energetic x-ray images are mathematically combined and processed to form a result. The result of processing the mono-energetic x-ray images is presented. The result comprises processed mono-energetic x-ray image data describing materials in the object with greater sensitivity, identifying the layers, and identifying the material composition than in the first image or the second image.

17 Claims, 6 Drawing Sheets

U.S. PATENT DOCUMENTS

| | | |
|---|---|---|
| 2004/0109532 A1 | 6/2004 | Ford et al. |
| 2004/0208276 A1 | 10/2004 | Kaufman |
| 2004/0213372 A1 | 10/2004 | Akagi |
| 2004/0218718 A1 | 11/2004 | Freudenberger et al. |
| 2005/0117705 A1 | 6/2005 | Morrison et al. |
| 2006/0204076 A1 | 9/2006 | Avinash et al. |
| 2007/0034805 A1 | 2/2007 | Hopkins et al. |

OTHER PUBLICATIONS

Lehmann et al., "Generalized Image Combination in Dual kVp Digital Radiography," Med. Phys. 8 (5), Sep./Oct. 1981, pp. 659-666.

Engler et al., "Review of Duel-Energy Computer Tomography Techniques," The American Society for Nondestructive Testing, Inc., Materials Evaluation, 48 May 1990, pp. 623-629.

Dobashi et al., "Development of Compact Hard X-ray Source Based on Laser-Electron Collision Using X-Band Linac", Proceedings of EPAC 2002, Paris France, pp. 677-679.

Carroll, "Tunable, Monochromatic X-Rays: An Enabling Technology for Molecular/Cellular Imaging and Therapy", Journal of Cellular Biochemistry, 2003. pp. 90: 502-508.

USPTO office action for U.S. Appl. No. 12/154,214 dated Dec. 28, 2009.

Schwartz, "Use of Tangential Radiography and Resonance Ultrasonic Techniques to Evaluate Bonding Quality", pp. 1-7, retrieved Jul. 21, 2009. http://www.ndt.net/article/wcndt2004/pdf/materials_characterization/304_schwartz.pdf.

Tritz et al., "Tangential soft x-ray imaging for shape and current profile measurements", Review of Scientific Instruments, vol. 74, No. 3, Mar. 2003, pp. 2161-2164.

Rousse et al., "Production of a keV X-Ray Beam from Synchrotron Radiation in Relativistic Laser-Plasma Interaction", The American Physical Society, vol. 93, No. 13, Sep. 2004, pp. 135005-1 to 135005-4.

Burkle, "Application of the Tangential Radiographic Technique for Evaluating Pipe System Erosion/Corrosion", Materials Evaluation/47/Oct. 1989, The American Society for Nondestructive Testing, Inc., pp. 1184-1188.

Burkle et al., "Burnoff and Film Latitude in the Tangential Radiographic Technique", Materials Evaluation/Nov. 1992, The American Society for Nondestructive Testing, Inc., pp. 1274-1277.

Viswanathan et al., "Performance Characteristics of Conventional X-Ray Generator, Isotope Source, and High-Energy Accelerator in Rocket Motor Evaluation", Materials Evaluation, Jan./Feb. 1987, American Society for Nondestructive Testing, Inc., pp. 86-90.

"Standard Guide for Radioscopy", ASTM International Designation: E1000-98 (Reapproved 2009), pp. 1-31.

Leemans et al., "GeV electron beams from a centimetre-scale accelerator", nature physics, vol. 2, Oct. 2006, pp. 696-699.

U.S. Appl. No. 12/512,184, filed Jul. 30, 2009, Gordon, III et al.

U.S. Appl. No. 12/145,214, filed Jun. 24, 2008, Parazzoli et al.

Dilmanian, "Computed Tomography with Monochromatic Xrays", American Journal of Physiological Imaging, 1992: 7 (3-4) 175-93.

USPTO final office action for U.S. Appl. No. 12/145,214 dated Mar. 26, 2010.

* cited by examiner $$I\bullet =\bullet \int I_0(E)e^{-\mu(E)x}dE \quad \overbrace{\phantom{XXXXXXXXXXXXXXXXX}}^{400}$$

$$I\bullet =\bullet \int I_0(E)e^{-[\mu_1(E)x_1+\mu_2(E)x_2+...+\mu_n(E)x_n]}dE \quad \overbrace{\phantom{XXXXXXXXXXXXXXXXXXXXXXXXXXX}}^{402}$$

$$404 \begin{cases} I(E_1)\bullet =\bullet I_0(E_1)\bullet e^{-(\mu_1(E_1)x_1+\mu_2(E_1)x_2+...+\mu_n(E_1)x)} \\ I(E_2)\bullet =\bullet I_0(E_2)\bullet e^{-(\mu_1(E_2)x_1+\mu_2(E_2)x_2+...+\mu_n(E_n)x)'} \\ \quad\quad\quad\quad\quad\quad\quad \vdots \\ I(E_n)\bullet =\bullet I_0(E_2)\bullet e^{-(\mu_1(E_2)x_1+\mu_2(E_2)x_2+...+\mu_n(E_n)x)} \end{cases}$$

$$406 \begin{cases} \mu_1(E_1)x_1+\mu_2(E_1)x_2+...+\mu_n(E_1)x\bullet =\bullet -\ln[I(E_1)/I_0(E_1)] \\ \mu_1(E_2)x_1+\mu_2(E_2)x_2+...+\mu_n(E_2)x\bullet =\bullet -\ln[I(E_2)/I_0(E_2)] \\ \quad\quad\quad\quad\quad\quad\quad \vdots \\ \mu_1(E_n)x_1+\mu_2(E_n)x_2+...+\mu_n(E_n)x\bullet =\bullet -\ln[I(E_n)/I_0(E_n)] \end{cases}$$

*FIG. 4*

MULTI-ENERGY RADIOGRAPHY USING MONOENERGETIC PULSED SOURCE

BACKGROUND INFORMATION

1. Field

The present disclosure relates generally to inspection and in particular to nondestructive inspection. Still more particularly, the present disclosure relates to a method and apparatus utilizing a plurality of mono-energetic, directional x-rays and the x-ray images of an object generated at multiple discrete x-ray energies to increase the sensitivity of nondestructive inspection of an object.

2. Background

A manufactured object may have sub-surface inclusions, fine porosity, or other anomalies that may make the structure unsuitable for its intended use. Therefore, nondestructive inspection of the object may be needed. Current nondestructive inspection techniques may include conventional polychromatic x-ray radiography, neutron radiography, and ultrasonic techniques. However, the current x-ray radiographic sensitivity in inspection is limited by the combination of the penetrating power of the x-ray, the polychromatic nature of the x-rays, and the scatter field intensity of the scattered radiation.

In addition, the detection of fine detail in material samples using conventional x-rays is often limited by the contrast available at the energy of the x-ray beam. This problem exists for inspection of large items, such as, without limitation, container inspection at ports, as well as inspection of small objects, such as castings for aerospace. Thus, it would be advantageous to have a method and apparatus that overcomes the problems of the limited sensitivity of non-destructive inspection.

SUMMARY

An embodiment of the present disclosure provides a method for multi-energy object inspection using a brilliant x-ray source. Using this x-ray source, a first mono-energetic x-ray image of an object at a first selected energy is generated. A second mono-energetic x-ray image of the object at a second selected energy is generated. The first selected energy is different than the second selected energy. The first mono-energetic x-ray image and the second mono-energetic x-ray image using a matrix to mathematically combine the first mono-energetic x-ray image and the second mono-energetic x-ray image is processed to form a result. The result of processing the first mono-energetic x-ray image and the second mono-energetic x-ray image is presented. The result comprises processed mono-energetic x-ray images data describing materials in the object with greater sensitivity, identifying the layers, and identifying the material composition which can not be determined from the first image or the second image individually.

In another embodiment, a brilliant x-ray inspection device is provided. The brilliant x-ray inspection device comprises a brilliant x-ray source and a data processing system. The brilliant x-ray source is capable of generating mono-energetic x-ray beams at multiple different discrete x-ray energies. The brilliant x-ray source generates a first mono-energetic x-ray image of an object at a first selected energy. The brilliant x-ray source generates a second mono-energetic x-ray image of the object at a second selected energy. The data processing system comprises a processor. The processor executes computer usable program code to process the first mono-energetic x-ray image and the second mono-energetic x-ray image of the object using a matrix to mathematically combine the first mono-energetic x-ray image and the second mono-energetic x-ray image to form a result, wherein the result comprises processed mono-energetic x-ray images data describing materials in the object with increased sensitivity, identifying the layers, and identifying the material composition which can not be determined from the first image or the second image individually.

The utilization of multi-energy radiography using brilliant x-rays for nondestructive inspection increases the sensitivity and material identification to fine detail of x-ray inspections. The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIG. 4 is a diagram illustrating mathematical equations for processing mono-energetic x-ray data in accordance with an advantageous embodiment;

DETAILED DESCRIPTION

Figure 1:
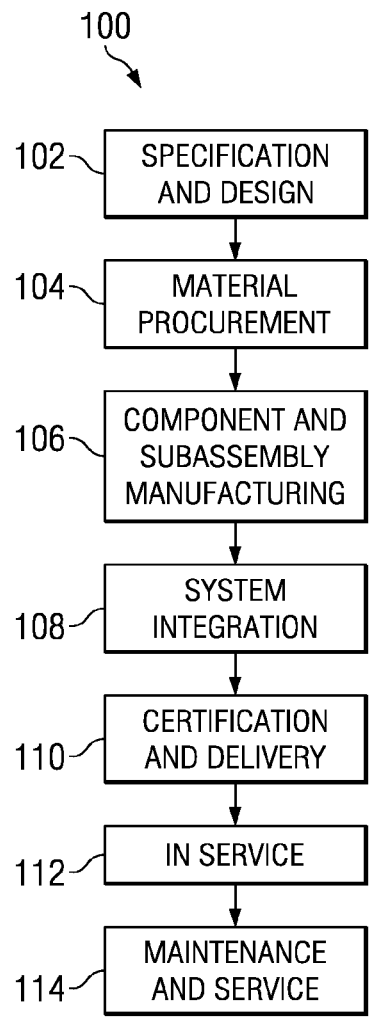
FIG. 1 is a diagram illustrating an aircraft manufacturing and service method in accordance with an advantageous embodiment.
Figure 2:
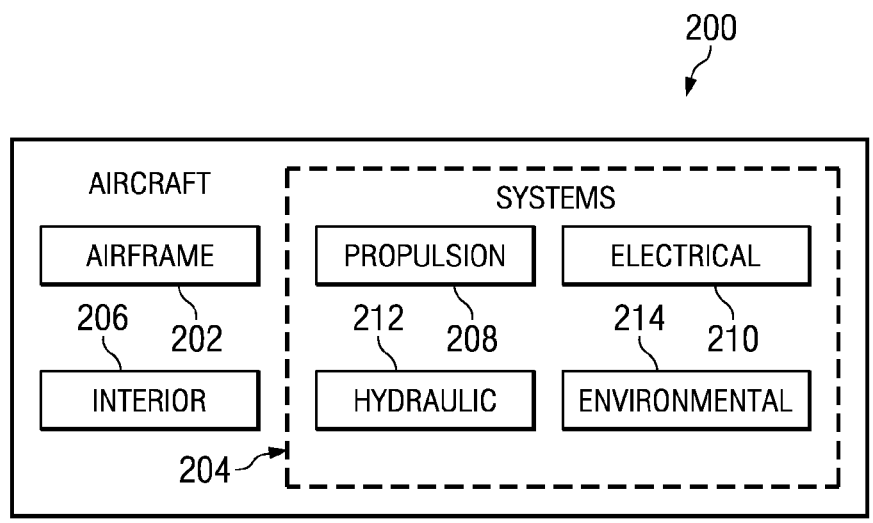
FIG. 2 is a diagram illustrating an aircraft in which an advantageous embodiment may be implemented.

Referring more particularly to the drawings, one embodiment of the disclosure may be described in the context of an aircraft manufacturing and service method 100 as shown in FIG. 1 and aircraft 200 as shown in FIG. 2. However, the advantageous embodiments are not limited to application to aircraft manufacturing and service methods.

Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104. During production, component and subassembly manufacturing 106 and system integration 108 of aircraft 200 in FIG. 2 take place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1. Also, one or more apparatus embodiments, method embodiments, or a combination thereof may be utilized during production stages, such as component and subassembly manufacturing 106 and system integration 108 in FIG. 1, for example, without limitation, by substantially expediting the assembly of, or reducing the cost of aircraft 200. Similarly, one or more of apparatus embodiments, method embodiments, or a combination thereof may be utilized while aircraft 200 is in service 112 or during maintenance and service 114 in FIG. 1.

Currently, x-ray inspection of objects typically uses the lowest energy available that offers sufficient penetration to image the internal condition of the object.

In conventional x-ray radiography, a user cannot select a single energy or wavelength for the x-rays to be produced. Instead, in conventional x-ray radiography, a range of x-ray energies are produced by a bremsstrahlung, polychromatic, x-ray source based on the maximum accelerating voltage (kV). For example, and without limitation, a conventional bremsstrahlung x-ray source may generate x-rays across an energy range of zero to four hundred-fifty kilo electron volts (0-450 keV) when the maximum accelerating voltage is 450 kV. Thus, the conventional x-ray beam may include, for example, some x-rays at energies less than one hundred kilo electron volts (100 keV), and x-rays at an energy of two hundred kilo electron volts (200 keV), three hundred kilo electron volts (300 keV), and a few x-rays up to four hundred-fifty kilo electron volts (450 keV).

The advantageous embodiments recognize that the detection of fine detail in material samples using conventional x-rays is often limited by the contrast available at the energy of the x-ray beam. Existing x-ray methods may suffer from a loss of sensitivity due to the scattered energies from the object and the polychromatic, spectral energy content of the x-ray beam from conventional bremsstrahlung sources. The use of bremsstrahlung sources at two energies has been demonstrated for some imaging, such as medical, but has never been practically effective, and is particularly non-effective at high energy levels (such as 1-10 MeV) because the existing sources simply cannot produce enough effective energy differential in the beams to provide a useful multi-energy calculation of material attenuation.

The embodiments recognize that at lower energies, the difference between Compton effects and photoelectric attenuation effects may only be exploited with significant difficulties due to the overlapping spectral content of the x-ray beam (using traditional sources). The Compton effect, also referred to as "Compton scattering", is the decrease in energy and corresponding increase in wavelength of an x-ray photon when it interacts with matter. Thus, when conventional x-rays interact with an object under inspection, Compton scattering leads to a decrease in the x-rays' energy and a decrease in the contrast of the x-ray image produced by the inspection process. Contrast refers to the ability to distinguish feature details arising from different x-ray attenuation properties, such as material thicknesses, atomic number, or density, in an image.

Also, with the polychromatic beams, the attenuation through an object may result in a shift or beam hardening of the x-ray spectra. This beam hardening effect limits the user's ability to calculate the material attenuation properties of the object.

These problems may exist for inspection of large items, such as, without limitation, container inspection at ports, as well as inspection of small objects, such as casting structures. A casting structure is any structure, unitized part, or other object that is produced using a casting process, such as, without limitation, investment casting, sand casting, or any other type of casting process. A casting structure may be titanium, titanium alloy, aluminum, aluminum alloy, copper, iron, steel, any other metal, any other metal alloy, ceramic, polymer, or any other substance. A casting structure may be, for example, and without limitation, a titanium aerospace part used in an aircraft, such as aircraft 200 in FIG. 2.

Fine porosity, shell inclusions, or other anomalies may sometimes occur below the surface of casting structure during the casting process. For example, the mold used during casting is typically coated with scale. Some of the scale material may find its way into the casting structure. The scale and any other substances that become absorbed into the casting structure during the casting process may form inclusions. These sub-surface anomalies may render a casting structure or other object unsuitable for its intended use and function. Therefore, it may be important to detect these anomalies using non-destructive evaluation techniques, such as x-ray inspection.

Therefore, in one advantageous embodiment of the present disclosure, a method for multi-energy object inspection using a brilliant x-ray source is provided. A brilliant x-ray source is a unique x-ray source that has a mono-energetic, narrow beam generated from a very small focal spot. A first mono-energetic x-ray image of an object at a first selected energy is generated. A second mono-energetic x-ray image of the object at a second selected energy is generated. The first selected energy is different than the second selected energy. The first mono-energetic x-ray image and the second mono-energetic x-ray image using a matrix to mathematically combine the first mono-energetic x-ray image and the second mono-energetic x-ray image is processed to form a result. A matrix is an array of data points. A digital image may be described as a matrix of data points, such as pixels.

For example, if a data point in a matrix of an image in the first image is 100 and the corresponding data point in a corresponding image in the second image is 90, then the images may be mathematically combined to generate a new image with the data point at a value of 10, where 90 subtracted from 100 provides the new data point value of 10.

The result of processing the first mono-energetic x-ray image and the second mono-energetic x-ray image is presented. The result comprises processed mono-energetic x-ray images data describing materials in the object with greater sensitivity, identifying the layers, and identifying the material composition which can not be determined from the first image or the second image individually.

Figure 3:
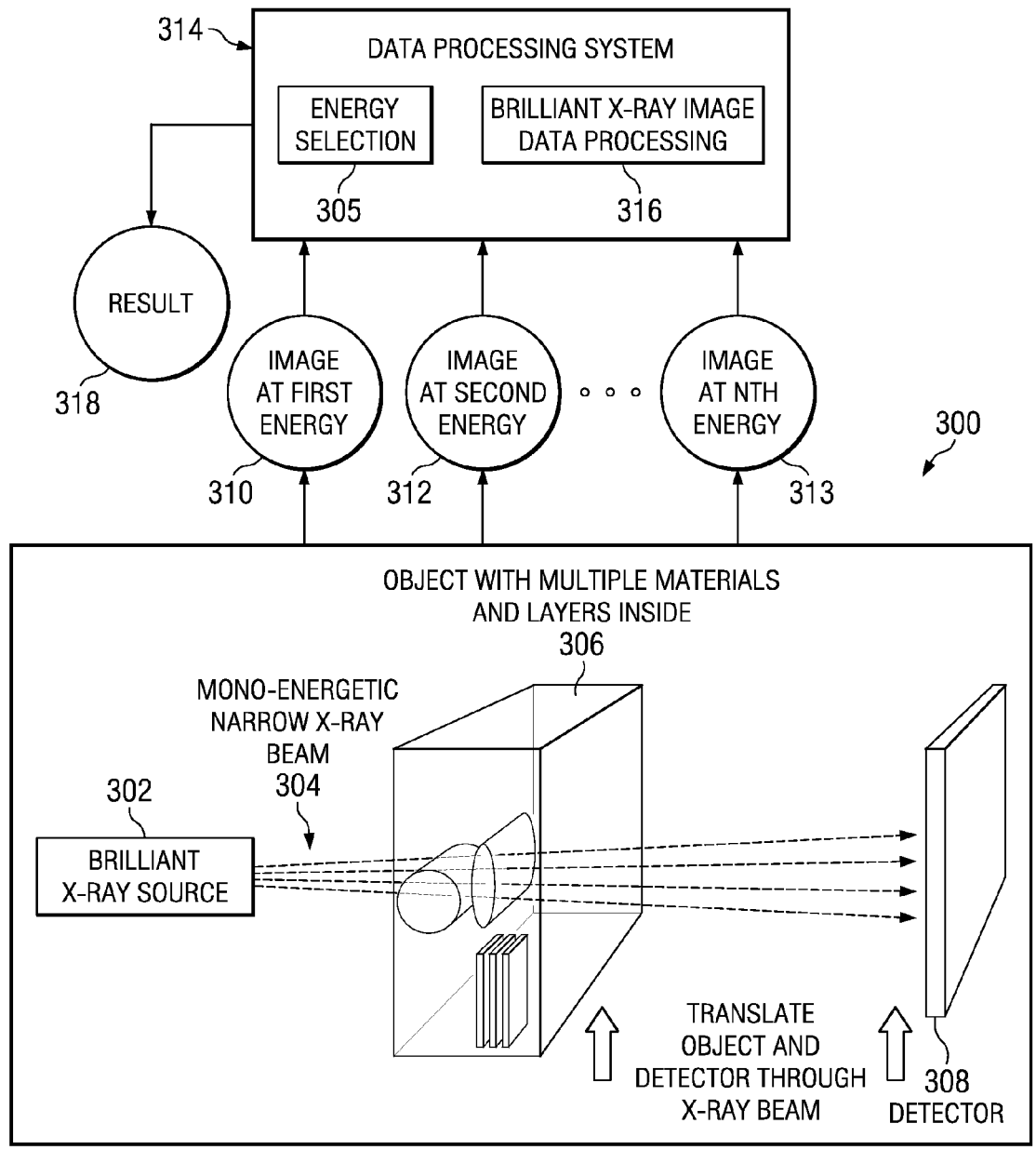
FIG. 3 is a diagram illustrating a brilliant x-ray inspection digital radiography device in accordance with an advantageous embodiment.

FIG. 3 is a diagram illustrating a brilliant x-ray inspection digital radiography device in accordance with an advantageous embodiment. Brilliant x-ray digital radiography inspection device 300 is a device for inspecting an object using multi-energy brilliant x-ray detection in a digital radiography configuration. Brilliant x-ray radiography inspection device 300 generates mono-energetic x-ray beams at a distinct, selected energy.

Brilliant x-ray digital radiography inspection device 300 may include part manipulators (not shown) for moving, translating, rotating, holding, or otherwise manipulating an object being inspected. These part manipulators may be implemented using any part manipulator devices and techniques that are currently available, or that become available in the future.

Brilliant x-ray source 302 is a device that generates mono-energetic, narrow x-ray beams 304 at a selected energy. The selected energy may be 10 kilo electron volts (keV), 25 keV, 50 keV, 200 keV, 400 keV, or any other energy level. The selected energy may be, without limitation, an energy in kilo electron volts (keV) or mega electron volts (MeV).

These mono-energetic, narrow beam x-rays may be referred to as brilliant x-rays. Brilliant x-ray source 302 may be implemented using any device for generating mono-energetic, narrow x-ray beams 304, such as, without limitation, a synchrotron source, high intensity laser source, or any other device capable of generating brilliant x-rays.

Brilliant x-ray source 302, in this example, generates brilliant x-rays in a short pulse at the selected energy using the inverse Compton effect. The inverse Compton effect increases the energy and decreases the wavelengths of photons upon interaction with matter, such as the interaction of a laser photon with an accelerated electron creating an x-ray photon at the selected energy.

Brilliant x-ray source 302 permits a user or energy selection 305 to select a single, specific energy at which mono-energetic, narrow x-ray beam 304 will be generated for the first energy 310. The user or energy selection 305 may then select a second, single, specific energy at which mono-energetic, narrow x-ray beams 304 will be generated for the second energy 312. This process may be continued iteratively "n" number of times 313 with the user and/or energy selection 305 selecting a different energy level and generating a different image of the object at the different selected energy. This ability to take an image at one or more energies, up to any number of specific selected energies, increases the sensitivity of the x-ray images produced by the brilliant x-ray inspection device, and allows for identifying the layers, and identifying the material composition, which can not be determined from the first image or the second image individually. A user may manually select an energy by using controls on brilliant x-ray source 302 or using any other method for making a selection, transmitting a selected energy level to brilliant x-ray source, or otherwise controlling brilliant x-ray source to generate x-rays at a particular energy. Energy selection 305 is software for selecting a specific energy level and providing the selected energy level to brilliant x-ray source 302. Energy selection 305 may use one or more default energies, a look-up table of energies, user pre-selected energy levels, or any other method for selecting an energy.

For example, a user or energy selection 305 may select mono-energetic, narrow x-ray beam 304 at 200 keV kilo-electron volts based on one or more known types of materials in object 306. Object 306 is an example of an object with multiple materials and/or layers inside. In such a case, brilliant x-ray source 302 will generate x-rays at only 200 kilo-electron volts rather than producing x-rays across a range of energies from zero to 450 kilo-electron volts.

A user may select a particular energy based on, without limitation, the type of object, the type of material in object 306, the number of layers of material in object 306, or any other criteria. In addition, with conventional, poly-energetic x-rays, there is a range of attenuation coefficients of the x-rays used that corresponds with the range of x-ray energies produced. However, with mono-energetic narrow x-ray beam 304, a single energy is selected and a single attenuation coefficient applies, therefore, an energy and a corresponding attenuation coefficient is selected based on the type of material in object 306 to control the sensitivity of the x-ray images produced by the brilliant x-ray inspection device.

In other words, a first energy, such as first energy 310, may be optimal for an object composed of titanium; a second energy, such as second energy 312, may be optimal for copper, and a third different energy for mono-energetic narrow beam x-ray may be optimal for an object composed of iron based on the attenuation coefficient. An object, such as object 306, may contain multiple layers or types of materials. For example, object 306 may contain both copper and iron. Multiple energies may be selected up to "n" number of times 313 in order to increase the sensitivity of the x-ray images produced for an object with multiple layers or materials.

It will be appreciated by one skilled in the art that the words "optimal", "optimize", "optimization" and related terms are terms of art that refer to improvements in sensitivity, inspection accuracy, identification of materials, identification of attenuation coefficients, and do not purport to indicate that an inspection or x-ray sensitivity is perfect, or is capable of achieving, an "optimal" or perfectly sensitive or accurate x-ray inspection state.

Object 306 may be any type of object composed of one or more types of materials having any number of layers. Object 306 may optionally be produced using a casting technique, such as, without limitation, investment casting, titanium investment casting, sand casting, or any other type of casting process.

For large objects composed of multiple layers, such as, without limitation, thick walled casting structures and/or objects having multiple layers of materials, mono-energetic, narrow beam x-rays 304 may be used to allow object 306 and detector 308 to be separated by a large distance, such that scatter does not affect the image quality or image contrast. Mono-energetic narrow x-ray beam 304 results in uniform attenuation coefficient "$\mu$" in the sample that can be identified by generating x-ray images at two or more different selected energies.

Mono-energetic narrow x-ray beam 304 is a narrow beam that may not cover an entire object or an entire portion of the object that is being inspected. Therefore, object 306 is rotated and translated during the x-ray process so that the entire object or all of a portion of the object that is being inspected is covered by mono-energetic narrow beam x-rays.

Detector 308 is a device for capturing mono-energetic narrow x-ray beams 304 that have interacted with object 306 and identify multiple materials or multiple layers of materials in the object based on the absorption and scatter of x-rays by the materials in the object. Detector 308 moves with object 306 as object 306 is rotated and/or translated. In other words, detector 308 is associated with object 306 such that detector 308 changes position as object 306 changes position. Detector 308 captures brilliant x-rays that interact with object 306 and generates data describing object 306 based on the x-ray energy detected by detector 308.

In this example, object 306 is positioned in a path of mono-energetic narrow x-ray beams 304. When mono-energetic narrow x-ray beams 304 are turned on, object 306 and detector 308 are moved simultaneously up and down, side to side, in the path of mono-energetic narrow x-ray beams 304. When the mono-energetic narrow x-ray beams 304 are shut off, the digital radiographer associated with brilliant x-ray digital radiography inspection device 300 analyzes the data generated by detector 308 and outputs a two-dimensional image of the object.

This data describing object 306, generated by detector 308 after monoenergetic, narrow x-ray beams 304 is generated at first energy 310, may be analyzed by data processing system 314, which is associated with brilliant x-ray digital radiography inspection device 300.

The data describing object 306 may optionally be transmitted to a remote computing device via a network connection for analysis by the remote computing device. The network may include, without limitation, a local area network (LAN), a wide area network (WAN), a virtual private network (VPN), an Ethernet, Internet, or any other type of network connection.

The user or software energy selection 305 then selects second energy 312 that is a different energy level than the first selected energy 310. Object 306 is positioned in the path of mono-energetic narrow x-ray beams 304 at the second selected energy. When mono-energetic narrow x-ray beams 304 are turned on, object 306 is moved up and down, side to side, in the path of mono-energetic narrow x-ray beams 304. When the mono-energetic narrow x-ray beams 304 beam is shut off, the digital radiographer associated with brilliant x-ray digital radiography inspection device 300 analyzes the data generated by detector 308 and outputs a two-dimensional image of the object and or a data set describing the results of the brilliant x-ray inspection to form image result 318 of the object.

The user may select a next energy and perform the x-ray inspection of the object at the next selected energy to form a next image of the object. This process may be continued iteratively "n" number of times with the user and/or energy selection 305 selecting a different energy level and generating a different image of the object at the different selected energy. In other words, in this example, only image at first energy 310 at a first selected energy and image at second energy 312 at a second selected energy are generated. However, a third image at a third selected energy, a fourth image generated at a fourth selected energy, or any other number "n" of images generated at any number "n" of different selected energy levels may be generated and used.

The images at each different selected energy level are then transmitted to data processing system 314. Data processing system 314 may be implemented by any type of computing device, such as, without limitation, a server, a client, a laptop computer, a desktop computer, a personal digital assistant (PDA), or any other type of computing device. Data processing system 314 may be implemented as a separate device than brilliant x-ray inspection device 300, as shown in FIG. 3, or data processing system 314 may be implemented as a computing device that is integrated into brilliant x-ray inspection device 300.

Brilliant x-ray image data processing 316 is software for mathematically combining two or more images generated using two or more different selected energies, such as the first image 310 and second image 312 to generate result 318. Result 318 may include, without limitation, an identification of material(s) in object 306, an identification of a number of layers of each material in object 306, an identification of attenuation coefficient(s) for materials in object 306, images of object 306 with enhanced quality to show fine detail and more detail than either the image at first energy 310 or the image at second energy 312.

In this manner, brilliant x-ray source 302 may be used to generate multiple images containing information on the material attenuation coefficient of object 306 at two or more different selected energies. By combining the multiple radiographic images at the two or more different selected energies mathematically, the sensitivity of the brilliant x-ray images to fine detail is enhanced and material identification is possible.

The object may then be moved so a different side or portion of the object is within the path of mono-energetic narrow x-ray beams 304. Mono-energetic narrow x-ray beams 304 may then be turned on and the object and detector moved simultaneously within the path of mono-energetic narrow x-ray beams 304 to generate another series of images at multiple energies of the object. This process of re-orienting the object and generating a new digital radiography image of the object at the selected energies may be repeated until the desired number of images has been generated.

In this example, the object 306 that is scanned by brilliant x-ray source 302 is a thick walled object with internal materials and layers. However, the embodiment shown in FIG. 3 may be used to scan any object using brilliant x-rays to obtain a more sensitive x-ray scan of the object. The embodiments are not limited to utilization on thick walled structures with internal materials and layers or aerospace objects.

FIG. 4 is a diagram illustrating mathematical equations for processing mono-energetic x-ray data sets in accordance with an advantageous embodiment. The mono-energetic x-ray beams generated by a brilliant x-ray source, such as brilliant x-ray source 302 in FIG. 3, makes the calculation of attenuation simpler.

Equation 400 is an equation for determining an attenuation coefficient for an object. Equation 400 is as follows:

$$I = \int I_o(E) e^{-\mu(E)x} dE$$

In equation 400, "I" is the measured intensity, "$I_o$" is the initial intensity of the x-rays' energy, "$\mu$" is the attenuation coefficient, "x" is the thickness of the material that is being inspected, "$I_o(E)$" is the initial intensity as a function of the energy spectrum, "$\mu(E)$" is the linear attenuation coefficient for the material as a function of the energy of the x-rays and x is the thickness of the material. The measured intensity is an integral over the energy spectra.

In an object that contains multiple materials the equation becomes quite complicated as shown in equation 402 which is as follows:

$$I = \int I_o(E) e^{-[\mu 1(E)x1 + \mu 2(E)x2 + \ldots + \mu n(E)xn]} dE$$

In equation 402, "$\mu 1(E)$", "$\mu 2(E)$" and "$\mu n(E)$" are the attention coefficients as a function of energy for materials 1, 2 through "n" and x1, x2 and xn are the thickness of the materials. Using variable peak energy bremsstrahlung spectra, the energies overlap and the spectra changes through the object, making the extraction of the materials from the data ineffective.

Sets of equations 404 are created for each image generated at each of the selected energies. Set of equations 404 is as follows:

$$I(E_1)=I_o(E_1)e^{-(\mu1(E1)x1+\mu2(E1)x2+\ldots+\mu n(E1)x)}$$

$$I(E_2)=I_o(E_2)e^{-(\mu1(E2)x1+\mu2(E2)x2+\ldots+\mu n(En)x)}$$

$$I(E_n)=I_o(E_2)e^{-(\mu1(E2)x1+\mu2(E2)x2+\ldots+\mu n(En)x)}$$

In set of equations 404, "μ1", "μ2", and "μn" are discrete values at each selected energy used to create each image. Sufficient independent equations can be generated by using appropriate mono-energetic brilliant x-rays to solve for the materials in the sample.

Set of equations 404 is converted to set of equations 406, which is as follows:

$$\mu1(E_1)x1+\mu2(E_1)x2+\ldots+\mu n(E_1)x=-\ln[I(E_1)/I_o(E_1)]$$

$$\mu1(E_2)x1+\mu2(E_2)x2+\ldots+\mu n(E_2)x=-\ln[I(E_2)/I_o(E_2)]$$

$$\mu1(E_n)x1+\mu2(E_n)x2+\ldots+\mu n(E_n)x=-\ln[I(E_n)/I_o(E_n)]$$

If "x1", "x2" through "xn" layers of thickness of the object are known, then a matrix solution may be applied to determine the attenuation coefficients and to identify the material represented. Similarly if the materials are known, the thickness of layers may be determined using these equations.

The equations in FIG. 4 are examples of equations that may be calculated by processing software, such as brilliant x-ray image data processing 316 in FIG. 3, to identify materials and properties of materials in an object. However, the embodiments are not limited to utilization of the equations shown. The embodiments may utilize any equations, processes, or methods for mathematically combining image at different mono-energetic x-ray energies to generate enhanced images of an object and/or increasing sensitivity of brilliant x-ray inspections.

Figure 5:
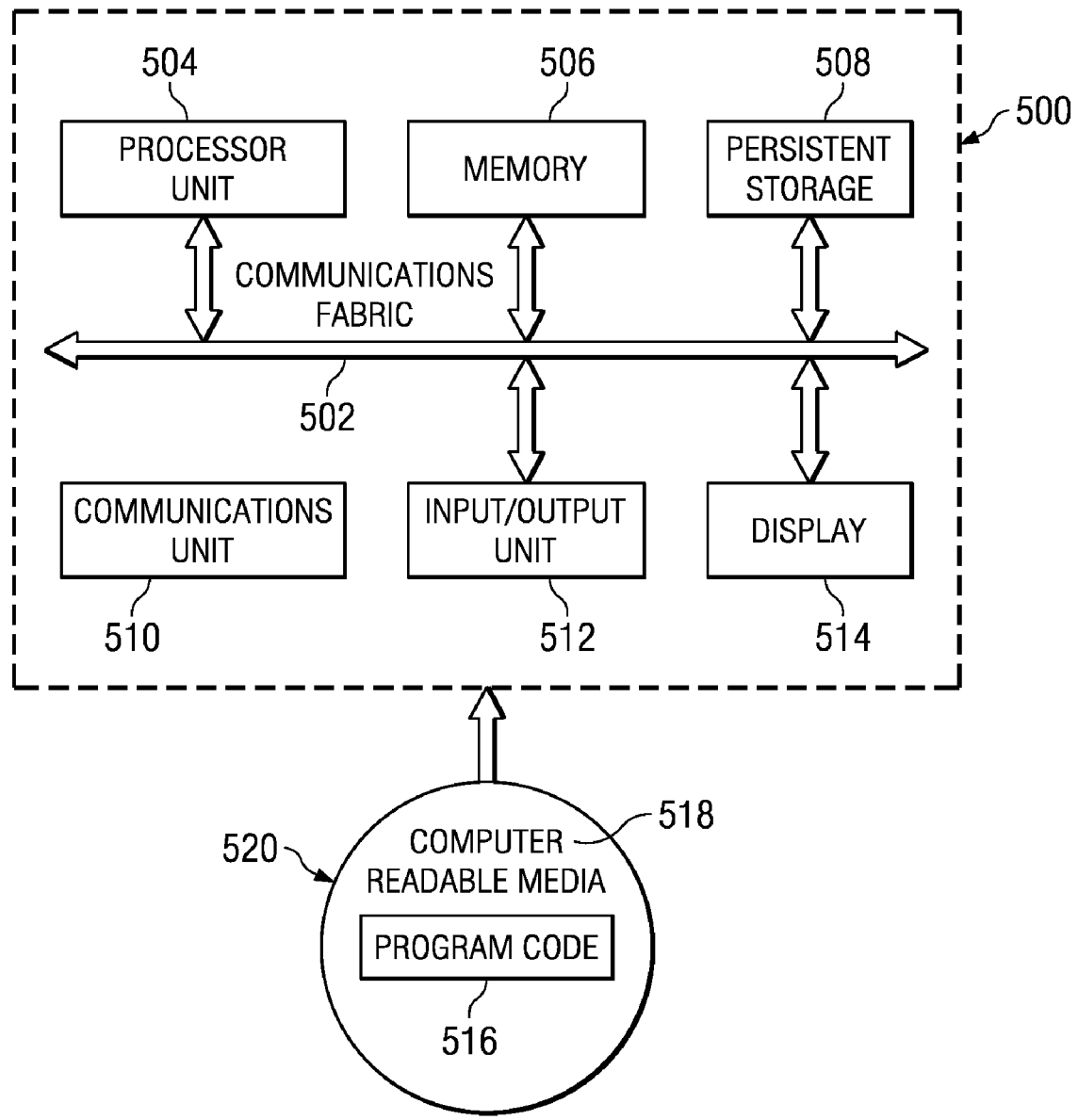
FIG. 5 is a diagram illustrating a data processing system in accordance with an advantageous embodiment.

With reference now to FIG. 5, a diagram illustrating a data processing system is shown in which advantageous embodiments may be implemented. Data processing system 500 is an example of a computer, such as a server, a client, or any computing device in which computer usable program code or instructions implementing the processes may be located for the illustrative embodiments. Data processing system 500 may be implemented as a desktop computer, a personal computer, a laptop computer, a personal digital assistant (PDA), a smart phone, or any other type of computing device, such as, without limitation, data processing system 314 in FIG. 3.

Data processing system 500 may be incorporated within a brilliant x-ray inspection device or receive image data from a brilliant x-ray inspection device, such as brilliant x-ray digital radiography inspection device 300 in FIG. 3. Data processing system 500 may receive data from a brilliant x-ray inspection device through a wired connection, through a wireless network connection, or from a removable data storage device, such as a flash memory or a memory stick that is plugged into a port associated with data processing system 500.

In this illustrative example, data processing system 500 includes communications fabric 502, which provides communications between processor unit 504, memory 506, persistent storage 508, communications unit 510, input/output (I/O) unit 512, and display 514.

Processor unit 504 serves to execute instructions for software that may be loaded into memory 506. Processor unit 504 may be one or more processors or may be a multi-processor core, depending on the particular implementation. Further, processor unit 504 may be implemented using one or more heterogeneous processor systems in which a main processor is present with secondary processors on a single chip. As another illustrative example, processor unit 504 may be a symmetric multi-processor system containing multiple processors of the same type.

Memory 506 and persistent storage 508 are examples of storage devices. A storage device is any piece of hardware that is capable of storing information either on a temporary basis and/or a permanent basis. Memory 506, in these examples, may be, for example, a random access memory or any other suitable volatile or non-volatile storage device. Persistent storage 508 may take various forms depending on the particular implementation. For example, persistent storage 508 may contain one or more components or devices. For example, persistent storage 508 may be a hard drive, a flash memory, a rewritable optical disk, a rewritable magnetic tape, or some combination of the above. The media used by persistent storage 508 also may be removable. For example, a removable hard drive may be used for persistent storage 508.

Communications unit 510, in these examples, provides for communications with other data processing systems or devices. In these examples, communications unit 510 is a network interface card. Communications unit 510 may provide communications through the use of either or both physical and wireless communications links.

Input/output unit 512 allows for input and output of data with other devices that may be connected to data processing system 500. For example, input/output unit 512 may provide a connection for user input through a keyboard and mouse. Further, input/output unit 512 may send output to a printer. Display 514 provides a mechanism to display information to a user.

Instructions for the operating system and applications or programs are located on persistent storage 508. These instructions may be loaded into memory 506 for execution by processor unit 504. The processes of the different embodiments may be performed by processor unit 504 using computer implemented instructions, which may be located in a memory, such as memory 506. These instructions are referred to as program code, computer usable program code, or computer readable program code that may be read and executed by a processor in processor unit 504. The program code in the different embodiments may be embodied on different physical or tangible computer readable media, such as memory 506 or persistent storage 608.

Program code 516 is located in a functional form on computer readable media 518 that is selectively removable and may be loaded onto or transferred to data processing system 500 for execution by processor unit 504. Program code 516 and computer readable media 518 form computer program product 520 in these examples. In one example, computer readable media 518 may be in a tangible form, such as, for example, an optical or magnetic disc that is inserted or placed into a drive or other device that is part of persistent storage 508 for transfer onto a storage device, such as a hard drive that is part of persistent storage 508. In a tangible form, computer readable media 518 also may take the form of a persistent storage, such as a hard drive, a thumb drive, or a flash memory that is connected to data processing system 500. The tangible form of computer readable media 518 is also referred to as computer recordable storage media. In some instances, computer recordable media 518 may not be removable.

Alternatively, program code 516 may be transferred to data processing system 500 from computer readable media 518 through a communications link to communications unit 510 and/or through a connection to input/output unit 512. The communications link and/or the connection may be physical or wireless in the illustrative examples. The computer readable media also may take the form of non-tangible media, such as communications links or wireless transmissions containing the program code.

The different components illustrated for data processing system 500 are not meant to provide architectural limitations to the manner in which different embodiments may be implemented. The different illustrative embodiments may be implemented in a data processing system including components in addition to or in place of those illustrated for data processing system 500. Other components shown in FIG. 5 can be varied from the illustrative examples shown.

As one example, a storage device in data processing system 500 is any hardware apparatus that may store data. Memory 506, persistent storage 508, and computer readable media 518 are examples of storage devices in a tangible form.

In another example, a bus system may be used to implement communications fabric 502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 506 or a cache such as found in an interface and memory controller hub that may be present in communications fabric 502.

Figure 6:
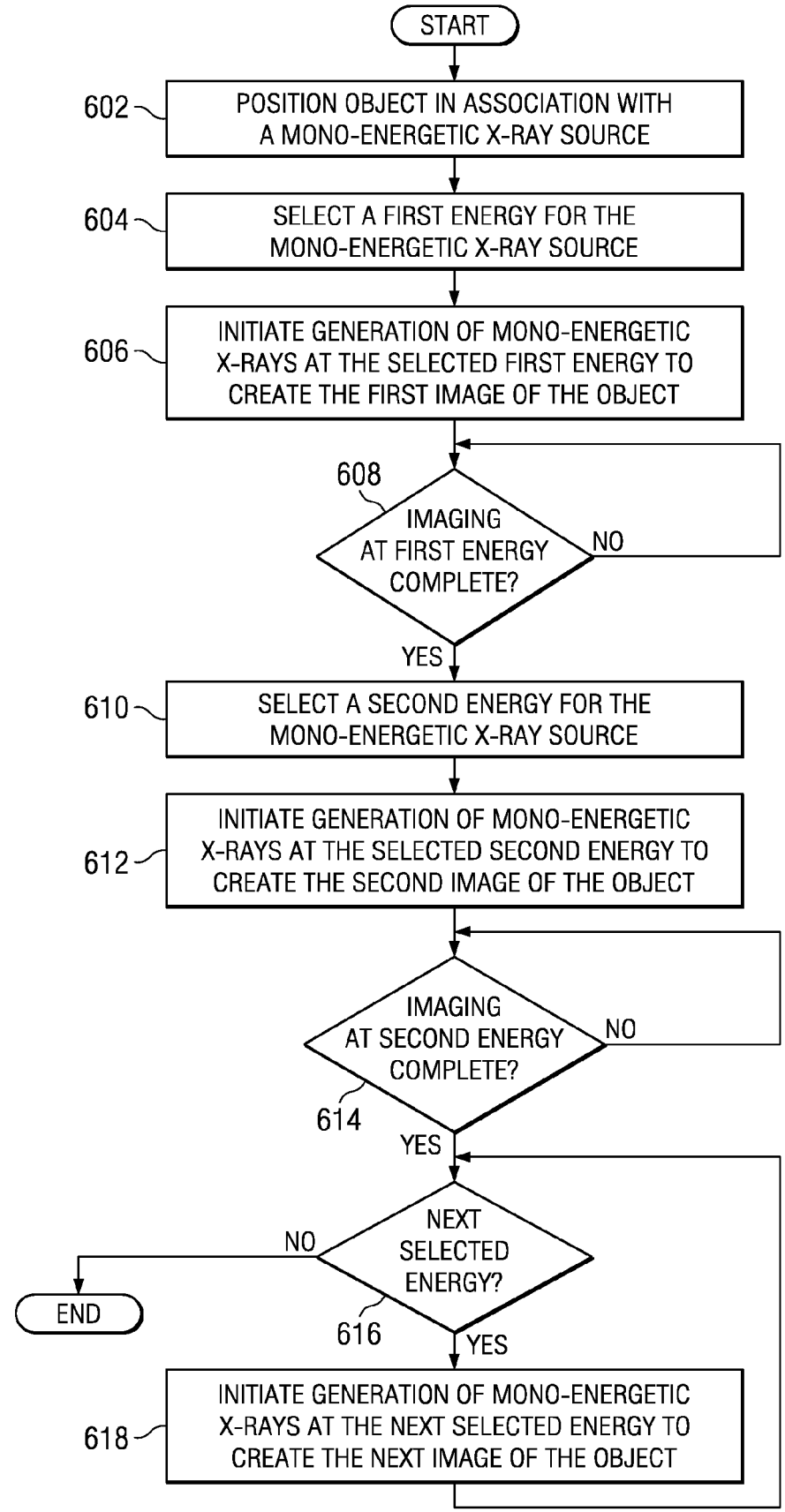
FIG. 6 is a flowchart illustrating a process for generating mono-energetic data for an object at multiple different selected energies in accordance with an advantageous embodiment.

Turning now to FIG. 6, a flowchart illustrating a process for generating mono-energetic data sets for an object at multiple different selected energies is shown in accordance with an advantageous embodiment. The process in FIG. 6 may be implemented by a user operating a brilliant x-ray inspection device, such as brilliant x-ray digital radiographic inspection device 300 in FIG. 3.

The process begins when a user positions an object to be inspected in association with a mono-energetic x-ray source, such as brilliant x-ray source 302 in FIG. 3 (operation 602). For example, the user may place the object in the path of the mono-energetic x-ray beams generated by the mono-energetic x-ray source.

A first energy for the mono-energetic x-ray source is selected (operation 604). Generation of mono-energetic x-ray beams at the selected first energy is initiated to generate a first image of the object (operation 606). The first image may include, without limitation, a single image, two or more images, one or more images of the entire object, and/or one or more images of a portion of the object. All of the images in the first image are generated using the mono-energetic x-ray beams at the first selected energy.

A determination is made as to whether imaging of the object at the first selected energy is complete (operation 608). When the imaging at the first selected energy is complete, a second selected energy for the mono-energetic x-ray source is selected (operation 610). The second selected energy is a different energy than the first selected energy. For example, and without limitation, if the first selected energy is 10 keV, the second selected energy may be 20 keV, 25 keV, or any other energy that is different than the first selected energy.

Generation of mono-energetic x-ray beams at the second selected energy is initiated to create a second image of the object (operation 612). Again, the second image may include a single image, two or more images, one or more images of the entire object, and/or one or more images of a portion of the object. All the data in the second image are generated using mono-energetic x-ray beams at the second selected energy.

A determination is then made as to whether imaging at the second selected energy is complete (operation 614). When imaging at the second selected energy is complete, a determination is made as to whether a next energy is selected (operation 616). A third energy may optionally be selected by the user to generate a third image. Likewise, a fourth energy, a fifth energy, or any number of additional energies may be selected for use in generating a fourth image, a fifth image, or any other number of additional images. Each image of the object is generated using a different selected energy. If a next energy is not selected, the process terminates thereafter.

If a next selected energy is selected, generation of mono-energetic x-ray beams at the next selected energy is initiated to create a next image of the object (operation 618). The process then returns to operation 616 to determine whether another different energy is selected (operation 616). When there are no additional different energies selected at operation 618 the process terminates thereafter.

Figure 7:
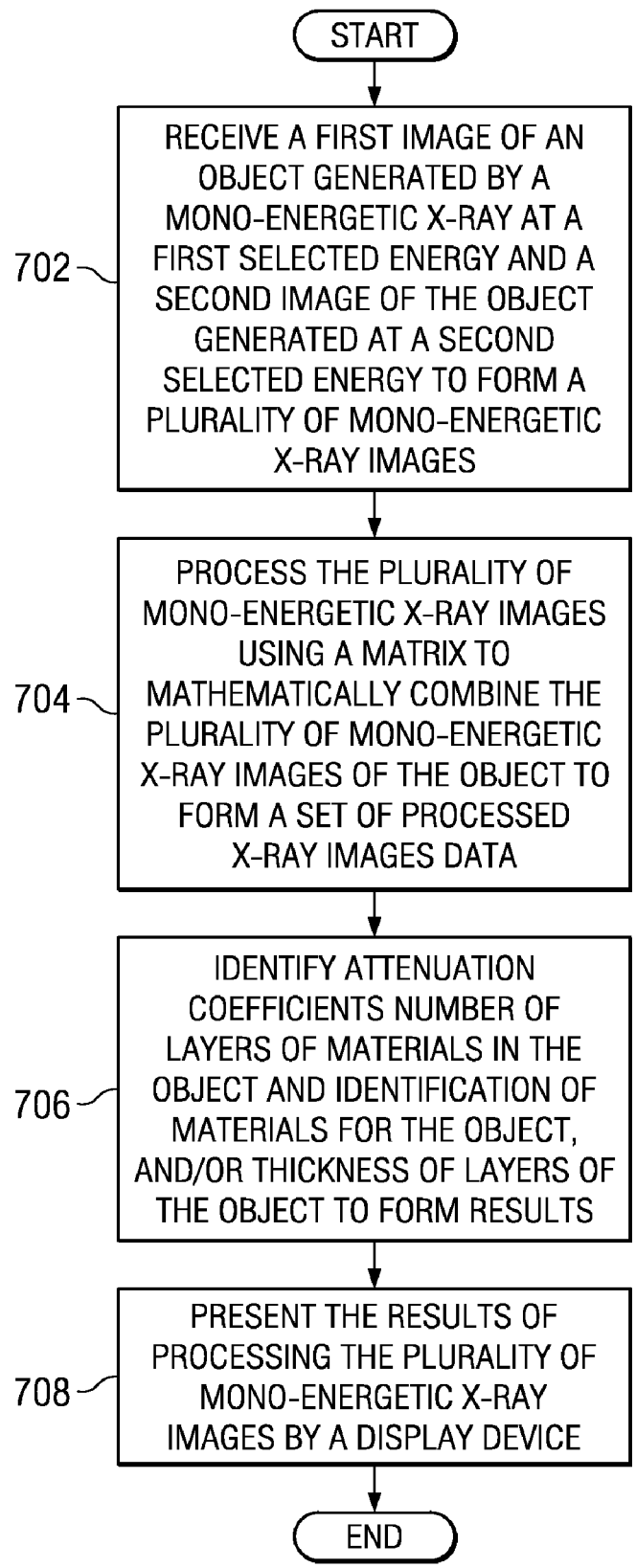
FIG. 7 is a flowchart illustrating a process for processing mono-energetic data sets for an object at multiple different selected energies in accordance with an advantageous embodiment.

FIG. 7 is a flowchart illustrating a process for processing mono-energetic data sets for an object at multiple different selected energies in accordance with an advantageous embodiment. The process in FIG. 7 is implemented by software for processing two or more images of an object generated using two or more different selected energies, brilliant x-ray image data processing 316 in FIG. 3.

The process begins when a first image of an object generated by a mono-energetic x-ray beams at a first selected energy and a second image of the object generated at a second selected energy are received to form a plurality of mono-energetic x-ray images (operation 702). The plurality of mono-energetic x-ray images are processed using a matrix to mathematically combine the plurality of mono-energetic x-ray images of the object to form a set of processed x-ray images data (operation 704). Attenuation coefficients, identification of materials in the object, identification of thickness of layers of the object, and/or identification of a number of layers of materials in the object are identified based on the set of processed x-ray images data (operation 706). The results of processing the plurality of mono-energetic x-ray images are presented by a display device (operation 708) with the process terminating thereafter.

The results may be presented in an audio format, a video or graphical format, an audio and video format, as a print out on a paper medium, or in any other format. The display device may be implemented as, without limitation, a speaker, a monitor, a touch screen, a printer, or any other output device. In one embodiment, the results may include a fine detail enhanced images that show fine details that may not be distinguishable on the first image or the second image.

In FIG. 7, only two images at two different x-ray energies are utilized. However, the process in FIG. 7 may also process three images generated at three different selected energies, four images generated at four different selected energies, or any other number "n" images generated at "n" different selected energies. Thus the multi-energy radiography method of FIG. 7 uses multiple brilliant x-ray images at multiple selected energy levels to improve fine detail in object x-rays and identify the attenuation coefficients of materials in the object.

Therefore, in one advantageous embodiment of the present disclosure, a method for multi-energy object inspection using a brilliant x-ray source is provided. A first mono-energetic x-ray image of an object at a first selected energy is generated. A second mono-energetic x-ray image of the object at a second selected energy is generated. The first selected energy is different than the second selected energy. The first mono-energetic x-ray image and the second mono-energetic x-ray image using a matrix to mathematically combine the first mono-energetic x-ray image and the second mono-energetic x-ray image is processed to form a result. The result of processing the first mono-energetic x-ray image and the second mono-energetic x-ray image is presented. The result comprises processed mono-energetic x-ray image data describing materials in the object with greater sensitivity than in the first image or the second image.

Multi-energy radiography using a brilliant x-ray source may be used to increase the sensitivity of inspections of object and improve sensitivity to fine detail in nondestructive inspections. The multi-energy brilliant x-ray inspection process enables improved identification of materials in an object, identification of attenuation coefficients for an object, and/or identifying the thickness of layers of materials in the object. The material content of the object may be identified using the x-ray attention coefficient(s) in the image(s) of the object.

Thus, the multi-energy brilliant x-ray radiography method and apparatus of the advantageous embodiments may be used, without limitation, to find particular material defects, such as shell inclusions in castings, with greater sensitivity than current technology and/or to eliminate overlaying features, such as wire mesh or lightning strike protection, in composite structure inspection to detect details in underlying material that would be otherwise obscured. The multi-energy radiography using brilliant x-rays may also be applied to large components to detect with greater accuracy the inclusion of such features as, without limitation, "O" rings and/or damage to internal features in auxiliary equipment, as well as detect material variations in cargo with greater accuracy than currently possible.

The multi-energy radiography method may be used in a variety of processes and fields, including, without limitation, security applications, aerospace manufacturing, casting processes, and industrial applications. For example, but without limitation, the multi-energy radiography method may be used in security applications to identify the contents of cargo containers, luggage, and sealed packages and containers. The multi-energy radiography may also be used to determine the quality of parts and components creating during manufacturing, such as, without limitation, casting structures.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for multi-energy inspection of an object using a brilliant x-ray source, the method comprising:
   processing a first mono-energetic x-ray image of an object at a first selected energy and second mono-energetic x-ray image of the object at a second selected energy, wherein the first selected energy and the second selected energy are selected from a number of energy levels;
   combining the first mono-energetic x-ray image and the second mono-energetic x-ray image to form a result;
   presenting the result, wherein the result comprises processed mono-energetic x-ray image data describing materials in the object;
   identifying an amount of a material in the object based on the processed mono-energetic x-ray image data; and
   identifying an attenuation coefficient of a material in the object based on the processed mono-energetic x-ray image data.

2. The method of claim 1 further comprising:
   identifying a type of material in the object based on the processed mono-energetic x-ray image data.

3. The method of claim 1 further comprising:
   identifying multiple materials in the object based on the processed mono-energetic x-ray image data.

4. The method of claim 1 further comprising:
   generating an enhanced image of the object based on the processed mono-energetic x-ray image data.

5. The method of claim 1 further comprising:
   generating an additional mono-energetic x-ray image of an object at an additional selected energy, wherein the additional selected energy is different then the first selected energy and the second selected energy;
   processing the first mono-energetic x-ray image, the second mono-energetic x-ray image, and the additional mono-energetic x-ray image using a matrix to mathematically combine the first mono-energetic x-ray image, the second mono-energetic x-ray image, and the additional mono-energetic x-ray image to form the result.

6. A method for multi-energy inspection of an object using a brilliant x-ray source, the method comprising:
   generating a first mono-energetic x-ray image of the object at a first selected energy;
   generating a second mono-energetic x-ray image of the object at a second selected energy;
   mathematically combining the first mono-energetic x-ray image and the second mono-energetic x-ray image using a matrix to form a enhanced x-ray image of the object, wherein the enhanced x-ray image of the object comprises processed mono-energetic x-ray image data describing materials in the object;
   identifying an amount of a material in the object based on the processed mono-energetic x-ray image data; and
   identifying an attenuation coefficient of a material in the object based on the processed mono-energetic x-ray image data.

7. The method of claim 6 wherein the object is an aircraft component.

8. A brilliant x-ray inspection device comprising:
   a brilliant x-ray source configured to generate mono-energetic x-ray beams at multiple different discrete x-ray energies, and wherein the brilliant x-ray source generates a first mono-energetic x-ray image of an object at a first selected energy, and wherein the brilliant x-ray source generates a second mono-energetic x-ray image of the object at a second selected energy, and wherein the brilliant x-ray source generates the mono-energetic x-ray beams in a short pulse at the first selected energy and the second selected energy using the inverse Compton effect; and
   a data processing system, wherein the data processing system comprises:
      a processor, wherein the processor executes computer usable program code to process the first mono-energetic x-ray image and the second mono-energetic x-ray image of the object and combine the first mono-energetic x-ray image and the second mono-energetic x-ray image to form a result, wherein the result comprises processed mono-energetic x-ray image data describing materials in the object.

9. The brilliant x-ray inspection device of claim 8 further comprising:
a display device, wherein the display device presents the result of processing the first mono-energetic x-ray image and the second mono-energetic x-ray image to a user.

10. The brilliant x-ray inspection device of claim 8 further comprising:
a detector, wherein the detector captures mono-energetic, directional x-rays having the first selected energy that have interacted with a region of the object and generates the first image of the object, and wherein the detector captures mono-energetic, directional x-rays having the second selected energy that have interacted with a region of the object and generates the second image of the object.

11. The brilliant x-ray inspection device of claim 8 wherein the processor executes computer usable program code to generate a enhanced image of the object based on the processed mono-energetic x-ray image data, wherein the features of the object are identified based on the enhanced image of the object.

12. The brilliant x-ray inspection device of claim 8 wherein the data processing system comprises a brilliant x-ray image data processing component, wherein the brilliant x-ray image data processing component identifies a type of material in the object based on the processed mono-energetic x-ray image data.

13. The brilliant x-ray inspection device of claim 8 wherein the data processing system comprises a brilliant x-ray image data processing component, wherein the brilliant x-ray image data processing component identifies a number of layers of a material in the object based on the processed mono-energetic x-ray image data.

14. The brilliant x-ray inspection device of claim 8 wherein the data processing system comprises a brilliant x-ray image data processing component, wherein the brilliant x-ray image data processing component identifies an attenuation coefficient of a material in the object based on the processed mono-energetic x-ray image data.

15. The brilliant x-ray inspection device of claim 8 wherein the brilliant x-ray source generates an additional mono-energetic x-ray image of an object at an additional selected energy, wherein the additional selected energy is different than the first selected energy and the second selected energy, and wherein the processor processes the first mono-energetic x-ray image, the second mono-energetic x-ray image, and the additional mono-energetic x-ray image and combines the first mono-energetic x-ray image, the second mono-energetic x-ray image, and the additional mono-energetic x-ray image to form the result.

16. The brilliant x-ray inspection device of claim 10 wherein the detector is a digital radiography detector, wherein the brilliant x-ray inspection device generates two-dimensional digital radiographic images of the object based on the brilliant x-ray data.

17. An apparatus comprising:
a bus system;
a communications system coupled to the bus system;
a memory connected to the bus system, wherein the memory includes computer usable program code; and
a processing unit coupled to the bus system, wherein the processing unit executes the computer usable program code to process a first mono-energetic x-ray image of an object at a first selected energy and second mono-energetic x-ray image of the object at a second selected energy and combine the first mono-energetic x-ray image and the second mono-energetic x-ray image to form a result; present the result of processing the first mono-energetic x-ray image and the second mono-energetic x-ray image, wherein the result comprises processed mono-energetic x-ray image data describing materials in the object; identify an amount of a material in the object based on the processed mono-energetic x-ray image data; and identify an attenuation coefficient of a material in the object based on the processed mono-energetic x-ray image data.

* * * * *